(12) United States Patent
Salton et al.

(10) Patent No.: US 10,229,563 B2
(45) Date of Patent: Mar. 12, 2019

(54) ILLUMINATED HANDLE FOR PORTABLE INSTRUMENTS

(71) Applicants: Scott Salton, Fremont, CA (US); Paul Newman, Fremont, CA (US); Rocco D. Pochy, Fremont, CA (US)

(72) Inventors: Scott Salton, Fremont, CA (US); Paul Newman, Fremont, CA (US); Rocco D. Pochy, Fremont, CA (US)

(73) Assignee: LIGHTHOUSE WORLDWIDE SOLUTIONS, INC., Fremont, CA (US)

( * ) Notice: Subject to any disclaimer, the term of this patent is extended or adjusted under 35 U.S.C. 154(b) by 0 days.

(21) Appl. No.: 15/479,976

(22) Filed: Apr. 5, 2017

(65) Prior Publication Data

US 2018/0293850 A1  Oct. 11, 2018

(51) Int. Cl.
*G08B 5/36* (2006.01)
*G08B 21/18* (2006.01)

(52) U.S. Cl.
CPC ............... *G08B 5/36* (2013.01); *G08B 21/18* (2013.01)

(58) Field of Classification Search
CPC .................................. G08B 5/36; G08B 21/18
See application file for complete search history.

(56) References Cited

U.S. PATENT DOCUMENTS

| | | | | |
|---|---|---|---|---|
| 4,634,294 A | * | 1/1987 | Christol | G01J 5/02 340/584 |
| 7,253,736 B2 | * | 8/2007 | Tethrake | G06K 19/07749 235/492 |
| 7,443,154 B1 | * | 10/2008 | Merewether | G01V 3/104 324/326 |
| 8,537,374 B2 | * | 9/2013 | Briggs | G01B 5/008 356/614 |
| 8,981,680 B2 | * | 3/2015 | Suda | B25F 5/021 315/314 |
| 9,126,317 B2 | * | 9/2015 | Lawton | B25B 21/00 |
| 2002/0050364 A1 | * | 5/2002 | Suzuki | B25B 21/02 173/1 |
| 2003/0193032 A1 | * | 10/2003 | Marshall | G01T 1/06 250/474.1 |
| 2005/0083676 A1 | * | 4/2005 | VanderSchuit | A23G 3/563 362/84 |
| 2008/0045802 A1 | * | 2/2008 | Brandstaetter | A61B 1/0607 600/199 |
| 2009/0114833 A1 | * | 5/2009 | Green | G01T 1/167 250/388 |
| 2011/0130632 A1 | * | 6/2011 | McGrail | A61B 1/00016 600/188 |
| 2012/0116267 A1 | * | 5/2012 | Kimball | A61B 17/00234 601/2 |
| 2013/0200159 A1 | * | 8/2013 | Webb | G06K 19/04 235/492 |

(Continued)

*Primary Examiner* — Adnan Aziz

(74) *Attorney, Agent, or Firm* — Michael L. Greenberg, Esq.; Greenberg & Lieberman, LLC

(57) ABSTRACT

A system and apparatus for indicating a status of an instrument via visible colored light is described. Status is preferably indicated according to which color is displayed on the apparatus, which is preferably configured to illuminate on or within the handle of the instrument. Statuses may be configured by the end user, or may be pre-established according to specific uses of the instrument.

2 Claims, 3 Drawing Sheets

(56) References Cited

U.S. PATENT DOCUMENTS

| | | | | |
|---|---|---|---|---|
| 2014/0035755 A1* | 2/2014 | Ward | ............ | G08B 5/00 |
| | | | | 340/691.1 |
| 2014/0053586 A1* | 2/2014 | Poecher | ............ | G01D 1/18 |
| | | | | 62/126 |
| 2014/0160261 A1* | 6/2014 | Miller | ............ | A61B 1/00052 |
| | | | | 348/77 |
| 2015/0077230 A1* | 3/2015 | Pochy | ............ | G08C 17/02 |
| | | | | 340/10.4 |
| 2015/0272575 A1* | 10/2015 | Leimbach | ............ | A61B 17/072 |
| | | | | 227/175.3 |
| 2015/0280424 A1* | 10/2015 | Leimbach | ............ | A61B 17/068 |
| | | | | 361/18 |
| 2016/0325391 A1* | 11/2016 | Stampfl | ............ | B25F 5/00 |
| 2017/0119391 A1* | 5/2017 | Schellin | ............ | A61B 17/105 |
| 2017/0239012 A1* | 8/2017 | Wood | ............ | A61B 90/361 |
| 2017/0340198 A1* | 11/2017 | Elazar | ............ | A61B 1/247 |

* cited by examiner

ILLUMINATED HANDLE FOR PORTABLE INSTRUMENTS

FIELD OF THE PRESENT INVENTION

The present invention relates generally status indicators for instruments, and more specifically relates to an illuminated handle on portable instruments that is configured to illuminate in order to indicate one or more status states.

BACKGROUND OF THE PRESENT INVENTION

A wide assortment of data collection instruments are known on the market today, many of which are configured for use by an individual holding the instrument in his or her hand. Such portable instruments are often configured to gather environmental data via one or more onboard environmental sensors.

Most indicators of conventional instruments are known to be disposed on the front of the unit, and are often present in the form of LEDs, screens, etc. Mechanisms such as these are not visible if the user walks around the instrument, or away from the instrument.

Conventionally, in order to provide such status visibility to the user of the instrument, a light stick (namely, a pole equipped with an illuminated status indicator) is often used in conjunction with a measuring instrument, such as a particle counter, to allow the status of the particle counter to be visible throughout the room. As with particle counters in a cleanroom, keeping the instrument easy to wipe down means eliminated extraneous projections from the instrument enclosure. Therefore, such a device would need to be equipped with indicators that are flush or disposed inside of the body of the instrument enclosure, such as within the handle of the instrument.

Thus, there is a need for an illuminated handle for portable data collection instruments that is configured to interface with the data collection process of the instrument itself, and display a color via at least one light embedded within the handle that corresponds to the status of the data collection instrument. Such a device is preferably integrated within the instrument, however some embodiments of the present invention may be configured to augment or replace an existing handle on a data collection instrument to afford the instrument the features of the present invention. Also by combining a "light stick" with a "handle" of the measuring instrument via the present invention, extraneous projection of light is eliminated, and the cost of use is reduced.

SUMMARY OF THE PRESENT INVENTION

The present invention relates to a new apparatus configured to provide a visible indication of the status of an instrument at a distance and from any direction. The apparatus of the present invention amounts to a visual indicator system which is preferably integrated within or attached to a handle of the instrument. At least one light is disposed within the handle, and is in communication with the sensor (s) of the instrument via internal wiring.

The lights are configured to illuminate, displaying a specific color and/or flashing sequence to indicate one or more statuses of the instrument. The placement of the at least one light within the handle of the instrument ensures that the status of the instrument is constantly visible to the user of the instrument, without the need to continually view a status screen, gauge, or monitor of the instrument in order to determine the present status of the instrument/sensors in real time. The illumination from the at least one light disposed in the handle of the instrument can preferably be seen from a distance, such that the user may easily know the status of the instrument, including ranged readings obtained by sensors of the instrument, even when he or she is no longer holding the instrument.

BRIEF DESCRIPTION OF THE DRAWINGS

The present invention will be better understood with reference to the appended drawing sheets, wherein.

DETAILED DESCRIPTION OF THE PREFERRED EMBODIMENT

The present invention is an apparatus configured to indicate the status of an instrument via colored light. More specifically, the present invention is a new form of data collection instrument configured to enable the user to determine the status of the instrument from any angle, and from a distance within a room. The present invention is a data collection instrument (10) which is equipped with a handle (20). The entirety of the handle (20) contains at least one light, referenced as lights (30), which are preferably embedded within the handle (20) of the present invention, such that they do not protrude out from the handle (20). As such, the blubs of the lights (30) are housed within or are flush with the enclosure of the instrument. The lights (30) are in communication with a light controller (40), which is housed within the instrument. The light controller (40) is configured to alter the color of the light emitted from the lights (30) according to the present status of the data collection instrument (10). The lights (30) are preferably oriented to cast light away from the handle (20) of the instrument (10), such that the user may detect the status of the instrument (10) from any angle or direction without having to physically approach the instrument (10) to determine its status.

The use of multiple colors by the present invention, emitted by the lights (30) within the handle (20), facilitates the remote viewing of the status of the instrument (10). For example, the color 'red' may indicate that an alarm is present during the measurement by the instrument (10), indicating an error of the sensor(s). Conversely, the lights (30) illuminating the color 'blue' may indicate that the sampling data is in progress by the instrument (10). The color 'Yellow' may be configured to indicate that the instrument (10) requires service and/or calibration. Similarly, the color 'green' emitted from the lights (30) may indicate that the instrument (10) is calibrated and ready for use. It is envisioned that lights assigned to varying statuses may vary according to the instrument (10) employing the system of the present invention.

Figure 1:
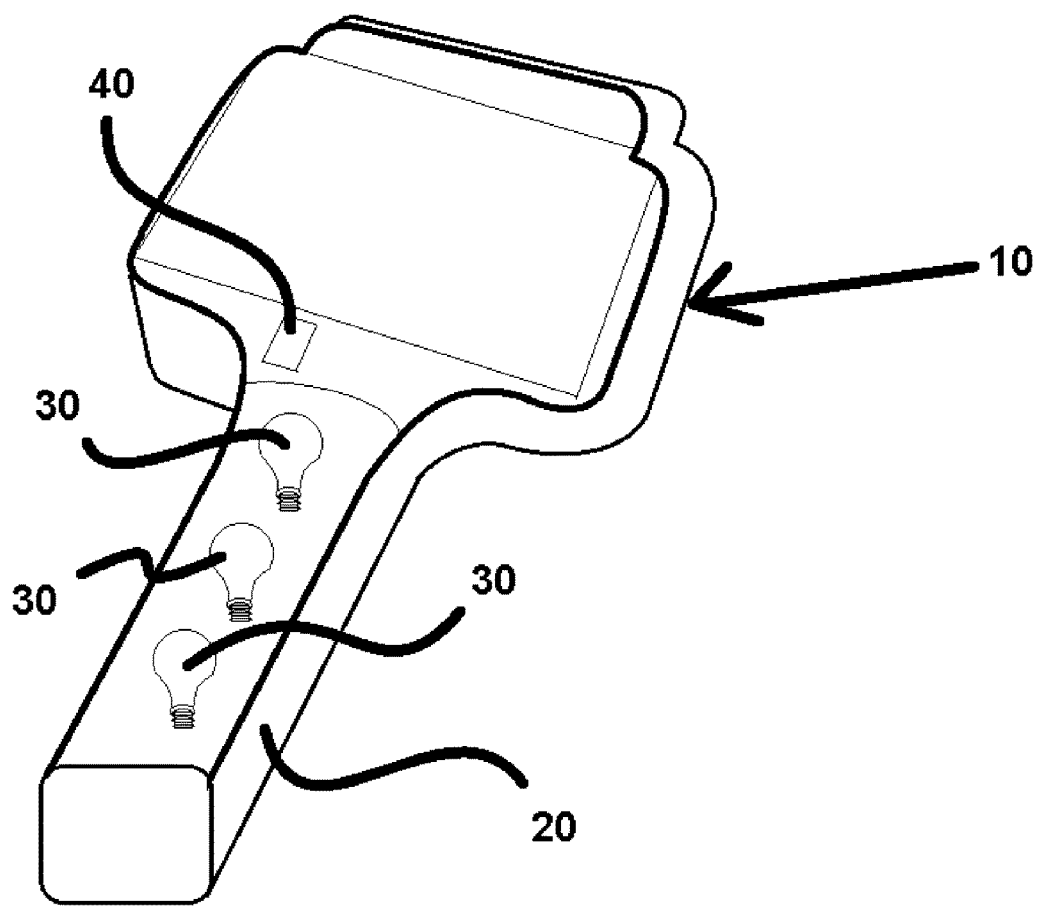
FIG. 1 exhibits a view of the present invention as seen from the front and side, installed on a data collection instrument.
Figure 2:
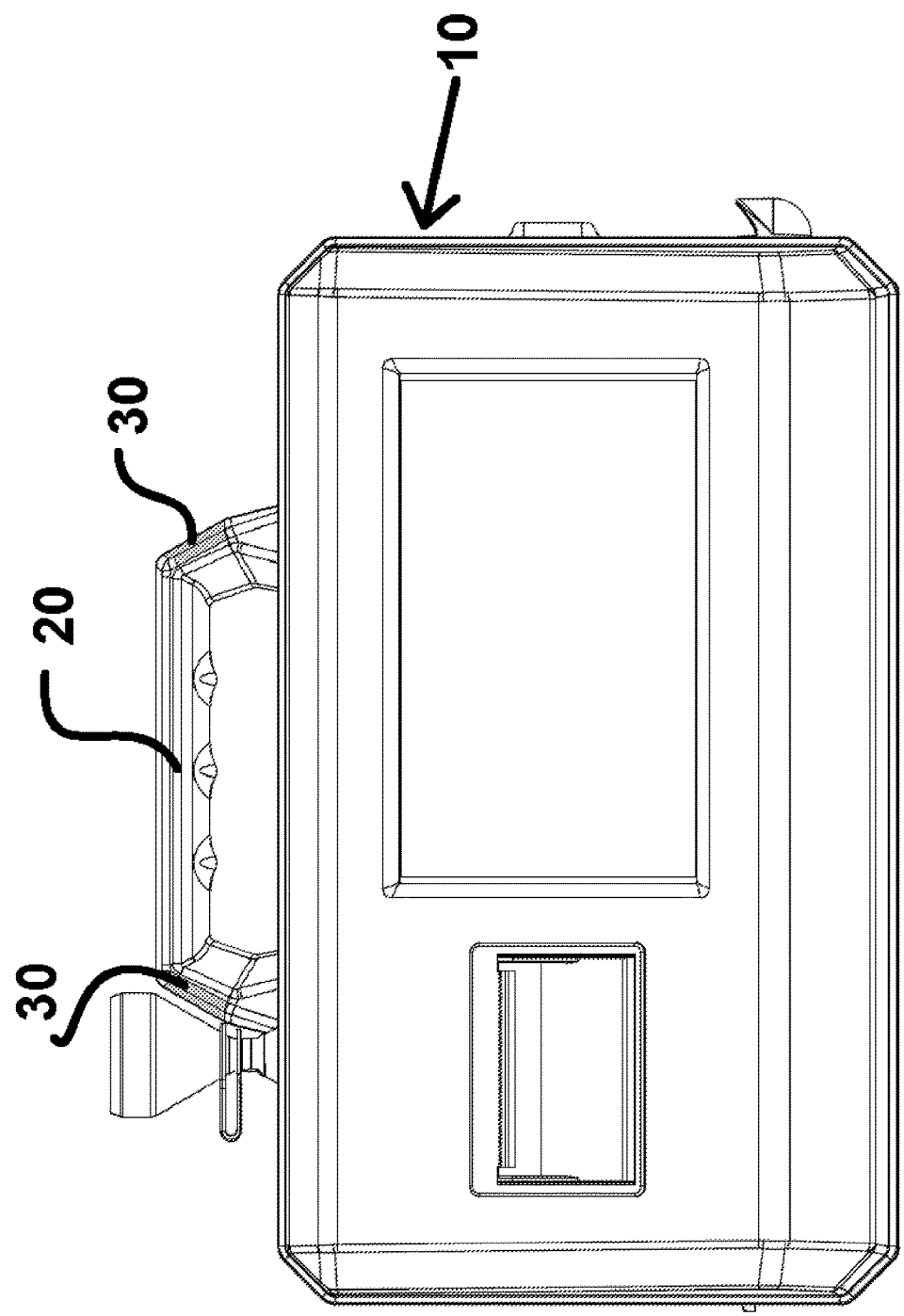
FIG. 2 shows a view of the present invention installed on a second environmental data collection instrument.

It should be noted that FIG. 1 and FIG. 2 depict example embodiments of the present invention, and the present invention is not limited to handle designs such as these. As such, the present invention may be incorporated on any format of handle used on data collection instrument, especially those used for gathering environmental data.

Preferred embodiments of the present invention are preferably equipped with multiple iterations of the lights (30) of the present invention. Such embodiments are preferably configured to illuminate the entirety of the handle (20) of the instrument with a uniform illumination. However, some embodiments of the present invention may be configured for integration within smaller instruments, and may only be equipped with a minimum singular light (30) of the present invention. In such cases, the light (30) is preferably still oriented such that it may illuminate a majority of the handle (20) during use.

In some alternate embodiments of the present invention, the lights (30) are disposed at the end(s) of the handle (20), such that the only the end(s) of the handle (20) are illuminated during use, such that the light remains visible while being carried by the user. Preferably, the entirety of the handle is illuminated by the lights (30), however some components of the handle may interfere with the uniform distribution of illumination within the handle. While the present invention is preferably integrated within the instrument, some embodiments of the present invention may be configured as a modular, add-on accessory to existing portable sensor instruments. In such cases, the present invention features a clip-on handle light and wiring, which enables the user to affix the clip-on handle light to the existing handle of the instrument, and connect it to the sensor of the instrument such that the lights (30) can indicate the status of the instrument during use.

The process of use of the present invention, as depicted in FIG. 2, is preferably as follows:

1. A user has a need to obtain measurement data via a portable environmental sensor instrument. (100)
2. The user obtains the portable environmental sensor instrument applicable to obtain the desired data; the instrument is equipped with the present invention. (110)
3. The user activates the instrument. (120)
4. Lights disposed within the handle of the instrument illuminate to inform the user of an initial status of the instrument. (130)
5. The lights illuminate a first color, indicating that the sensors of the instrument must be calibrated and/or serviced. (140)
6. The user calibrating and/or servicing the instrument. (150)
7. The lights within the handle of the instrument displaying a second color, the second color indicating a 'ready for use' status. (160)
8. The user taking a reading with the instrument. (170)
9. The lights illuminating a third color, indicating to the user the status of 'reading in progress.' (180)
10. The user observing the lights to obtain the status. (190)
11. The lights illuminating a fourth color, indicating to the user the status of 'reading complete.' (200)
12. The user obtaining and recording the needed measurement data. (210)

Figure 3:
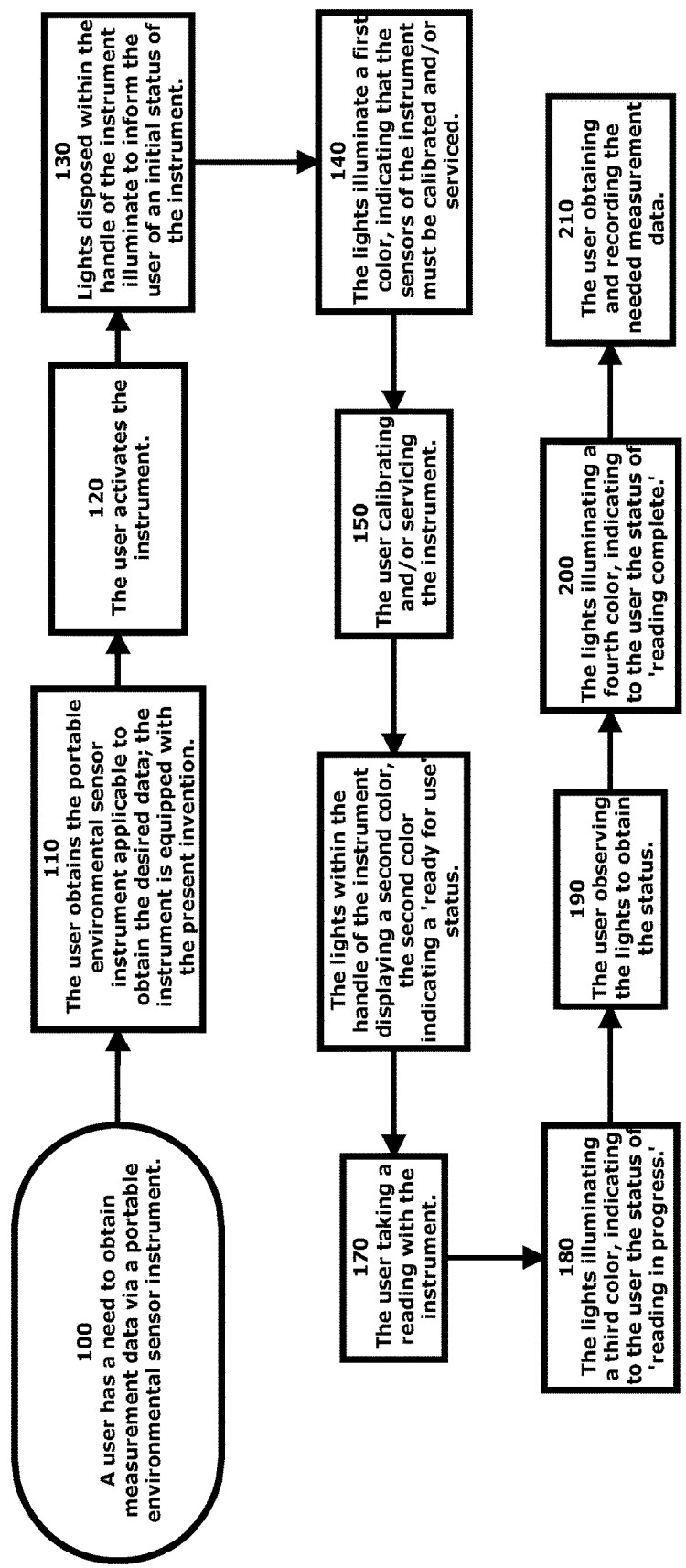
FIG. 3 depicts a flow chart detailing the process of use of the present invention.

It should be noted that the flow chart disclosed in FIG. 3 shows an example of use of the present invention, and details why having a visible status indicator disposed on the handle of an instrument is valuable to users, however it should be understood that the disclosed scenario of FIG. 3 is not the only application of the present invention. Additionally, it should be understood that the portable instrument equipped with the present invention includes any instrument that a human can carry from a first location to a second location.

Having illustrated the present invention, it should be understood that various adjustments and versions might be implemented without venturing away from the essence of the present invention. Further, it should be understood that the present invention is not solely limited to the invention as described in the embodiments above, but further comprises any and all embodiments within the scope of this application.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The exemplary embodiment was chosen and described in order to best explain the principles of the present invention and its practical application, to thereby enable others skilled in the art to best utilize the present invention and various embodiments with various modifications as are suited to the particular use contemplated.

We claim:

1. A visual status indicator for an environmental instrument, the environmental instrument having at least one sensor, comprising:
    a handle, said handle having an enclosure;
    wherein said handle is disposed on the environmental instrument;
    wherein said handle is configured to be held by one hand of a user;
    at least one light element, said at least one light element disposed within said enclosure such that said at least one light element is embedded within said handle to not protrude out from said handle so as to not gather particles from an environment;
    wherein said enclosure is semi-transparent and configured such that a majority of said handle is illuminated during use with said at least one light element and allow observation of a status of the environmental instrument from a location remote of the environmental instrument;
    a light controller, said light controller in communication with said at least one light element;
    wherein said light controller is in communication with the at least one sensor;
    wherein said at least one light element is configured to illuminate a first color when the at least one sensor requires calibration;
    wherein said at least one light element is configured to illuminate a second color when the at least one sensor is ready for use; and
    wherein said at least one light element is configured to illuminate a third color to indicate findings from the at least one sensor.

2. The visual status indicator for an environmental instrument of claim 1, wherein said light controller is in communication with a power supply of the environmental instrument.

* * * * *